United States Patent
Pan et al.

(10) Patent No.: US 6,988,990 B2
(45) Date of Patent: Jan. 24, 2006

(54) AUTOMATIC ANNOTATION FILLER SYSTEM AND METHOD FOR USE IN ULTRASOUND IMAGING

(75) Inventors: Lihong Pan, Brookfield, WI (US);
John T. Doherty, Grafton, WI (US);
Laurence M. Yudkovitch, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 244 days.

(21) Appl. No.: 10/447,350

(22) Filed: May 29, 2003

(65) Prior Publication Data

US 2004/0242998 A1   Dec. 2, 2004

(51) Int. Cl.
*A61B 8/00* (2006.01)
(52) U.S. Cl. ..................................... 600/437
(58) Field of Classification Search ........ 600/407–472; 73/625–626; 345/157, 171; 703/11; 704/1, 704/208, 260, 276; 128/916, 925; 367/7, 367/11, 130, 138
See application file for complete search history.

(56) References Cited

U.S. PATENT DOCUMENTS

| 5,545,654 A | 8/1996 | Macher |
| 2003/0036411 A1 * | 2/2003 | Kraft ........................... 455/566 |
| 2003/0055655 A1 * | 3/2003 | Suominen .................... 704/276 |
| 2004/0015079 A1 * | 1/2004 | Berger et al. ................ 600/437 |

* cited by examiner

*Primary Examiner*—Ali Imam
(74) *Attorney, Agent, or Firm*—Henry Policinski; Joseph S. Heino; Patrick M. Bergin

(57) ABSTRACT

The present invention provides a method and system for using the computer keyboard and/or speech recognition technology to automatically fill an image annotation during an ultrasound scan. More specifically, it provides a method and a system for annotating a displayed ultrasound image using commands that is comprised of; providing an annotation vocabulary sorted in descending order of usage frequency providing a method to select a subset of words from the vocabulary that are relevant to the imaged anatomy, detecting the initial command, selecting a suggestion list from the selected sub-vocabulary, and displaying the suggestion list to the user for optional acceptance or further specification.

26 Claims, 9 Drawing Sheets

AUTOMATIC ANNOTATION FILLER SYSTEM AND METHOD FOR USE IN ULTRASOUND IMAGING

FIELD OF THE INVENTION

The present invention relates generally to ultrasound imaging methods and systems. More specifically, it relates to a method and system for using the computer keyboard and/or speech recognition technology to automatically fill in an image annotation during an ultrasound scan.

BACKGROUND OF THE INVENTION

During a typical ultrasound scan, the sonographer frequently needs to type in an annotation on the image to indicate the anatomy scanned, probe orientation on the patient, and any abnormal anatomic feature in the image. The image, together with the superimposed annotation, is saved for later review and further diagnosis by a physician. That image and annotation becomes part of the patient's medical record.

During the scanning process, the sonographer maintains the ultrasound probe on the patient with one hand, while controlling the machine with the other hand. Thus, annotations are typically typed with only one hand. This is a difficult and awkward process at best. For example, it can be difficult for the sonographer to reach the keyboard while keeping the probe properly positioned on the patient, particularly during interventional procedures. Even with the ability to freeze-frame and cine the image, this remains a cumbersome procedure. If less typing would be required, or if typing can be done away with entirely, the situation would be more manageable. What is needed is a method and system whereby the sonographer uses a minimal amount of effort to complete the annotation by means of the computer keyboard during the examination. What is also needed is such a method and system whereby annotations are set according to a pre-programmed scheme depending upon the examination that is being performed.

In the experience of these inventors, several methods exist for voice-controlling the ultrasound equipment itself. However, previous voice recognition systems are used only to control or to select ultrasound system parameters. What is needed is a voice control method that recognizes common annotations used by ultrasound operators and that can be used in conjunction with or in place of keyboard annotation systems for the ultrasound equipment.

BRIEF SUMMARY OF THE INVENTION

Currently, to type an annotation, the sonographer types the text he or she wants to appear character by character. These inventors sought to maintain this mental model for the user. To make it simpler for the user, the method of the present invention is used to predict the complete word that the user intended to type. The most likely word to complete the letters already typed is displayed in lighter letters. Additionally, a "drop down" shows other options that the user may intend. To accept the most likely word, i.e. the one displayed in line with the typed letters, the user need only hit the confirmation button. The confirmation button can be the space bar, the return key, the set key, or any other key of the user's choosing. To select one of the "drop down" options, the user must use an arrow key to select one of the options, and then hit the confirmation button. At this point, the user is ready to type the next word. The system will suggest words most likely to follow the previous word selected. The user can either confirm one of the selected words, or continue to type the word he or she wants. The system will function as described previously following each letter typed. To get the system to work, it requires a list of words and associated frequency. Assuming this list is sorted by frequency, to get the algorithm to display the most likely word involves displaying the first word (of highest frequency) that matches all of the letters currently typed. The next best guesses can be added by listing the next x (let's say 4) highest frequency words with matching letters. This frequency list can be updated dynamically based on what annotations are actually typed, or the user can manually update the list. The system should also store a list of word-pairs. It uses this list to suggest the second word. This list can also be updated dynamically based on the user's history.

In short, the method and system of the present invention enables the keyboard to be used in such a way that the computer software completes the annotation of words by recognizing words of common usage in accordance with a pre-programmed scheme. The method and system of the present invention also enables the ultrasound operator to perform difficult examinations without requiring the operator to use the keyboard to fully type in the annotation in order to annotate images generated by the ultrasound equipment. That is, the operator is not required to type each and every letter of each and every word of the annotation. The method and system instead recognizes words that are frequently used in a particular scan and anticipates the word or words that the operator wants to complete. This capability simplifies difficult examinations, and reduces the occupational health problems from scanning in physically awkward situations. The present invention is also capable of employing both keyboard and speech recognition equipment to automatically fill in the annotation during ultrasound imaging.

The foregoing and other features of the method of the present invention will be apparent from the detailed description that follows.

DETAILED DESCRIPTION OF THE INVENTION

Figure 1:
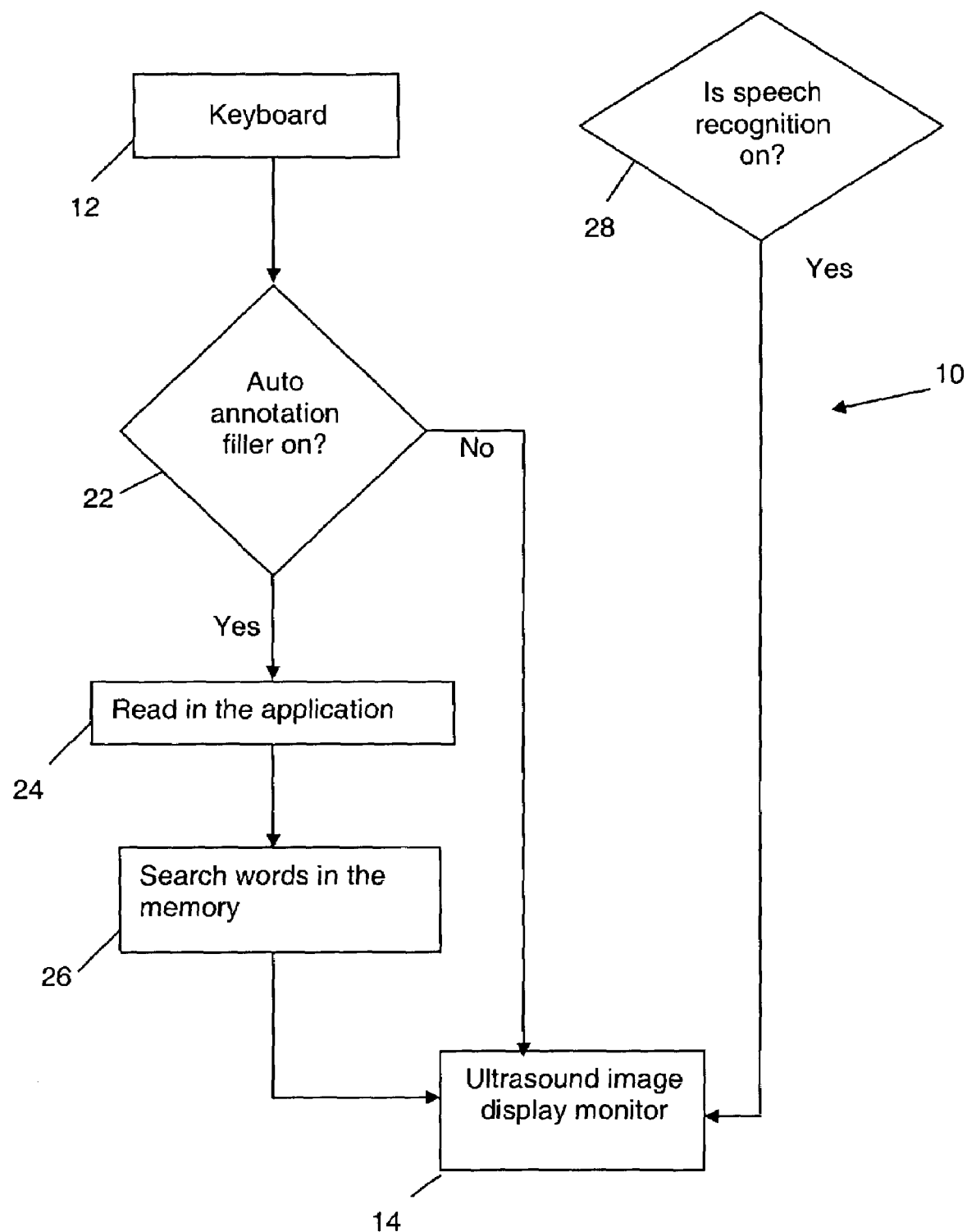
FIG. 1 is a schematic diagram of the automatic annotation filler method of the present invention.
Figure 2:
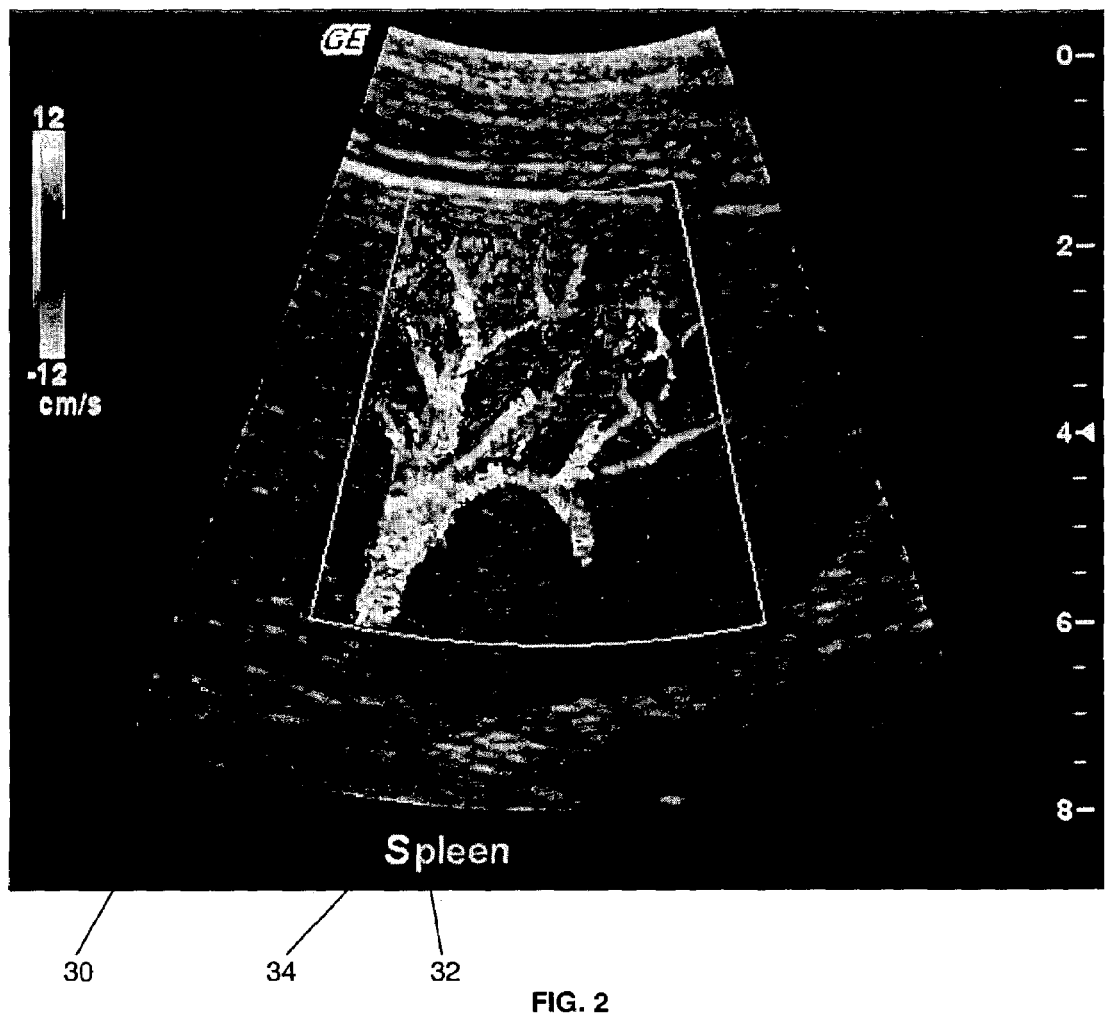
FIG. 2 is an example of a screen display employing the annotation filler of the present invention and showing the first letter completed by the user and the annotation filled by that letter.
Figure 3:
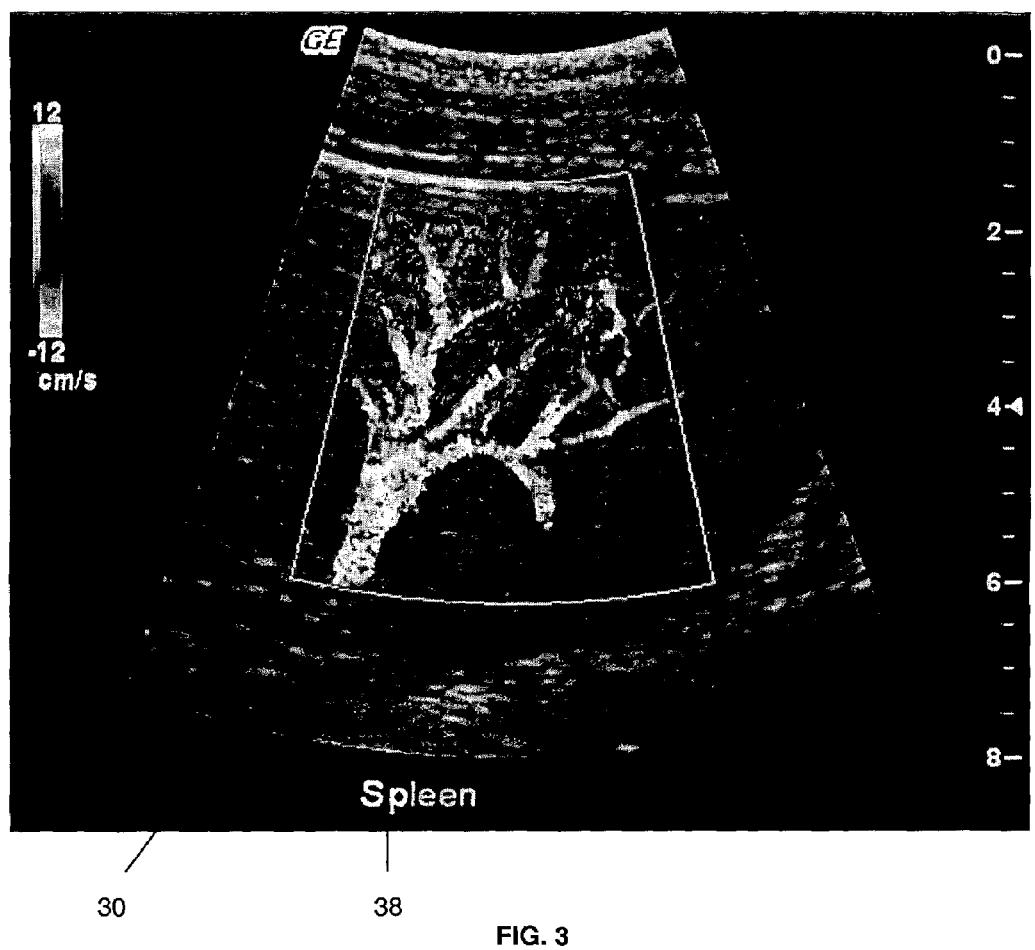
FIG. 3 is the screen display illustrated in FIG. 2 and showing the second letter completed by the user.
Figure 4:
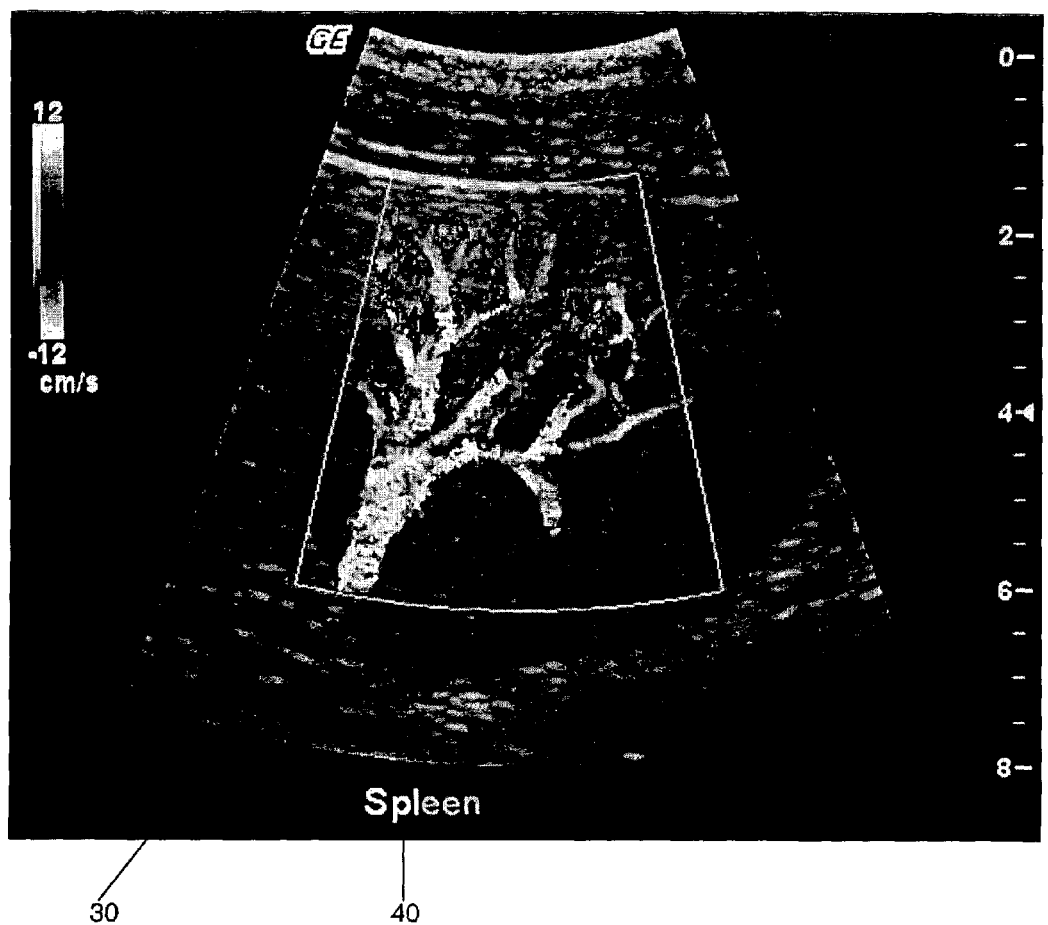
FIG. 4 is the screen display illustrated in FIG. 2 and showing the third letter completed by the user.
Figure 5:
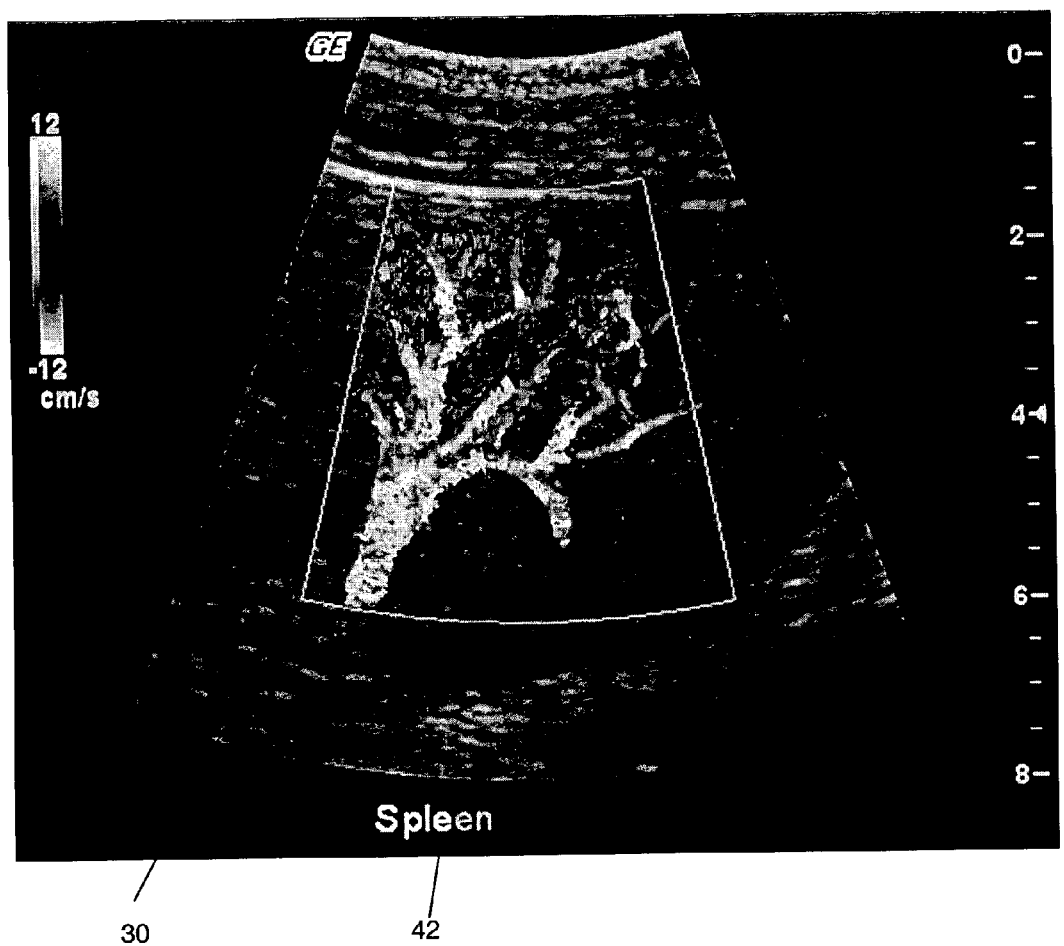
FIG. 5 is the screen display illustrated in FIG. 2 and showing the fourth letter completed by the user.

Ultrasound image annotation typically uses acronyms and abbreviations to identify or label anatomical landmarks, positions, locations or medical procedures. For example, the letters CBD stand for "Common Bile Duct", and the letters TRV stand for "Transverse." In ultrasound imaging, the system parameters are optimized depending on certain applications. Before starting to scan, the user should select the right application by pressing a key or button to preprogram the ultrasound system. For example, when scanning a patient's carotid artery, the user should select the "carotid" application to set the system parameters, and then begin the ultrasound scan. This maximizes system parameters for that particular type of scan.

In the method and system of the present invention, a keyboard is used to identify certain words that are most often used in ultrasound image annotations. This would include acronyms and abbreviations that are saved in a memory. The words should be grouped under each application. Some words may appear under multiple applications. For example, the abbreviations SAG (for "sagittal") and TRV appear under almost every type of ultrasound application. The words are listed by frequency. This concept, for example, can be demonstrated in a carotid application where the following Table 1 illustrates some of the words used for annotation purposes. Those words are saved in the memory, and in order, using the hierarchy as described above:

TABLE 1

Art (artery),
Aneur (aneurysm),
Anast (anastamosis)
AoAr (aortic arch),
Bifurcation
Bulb
CCA (common carotid artery),
Distal
ECA (external carotid artery),
EJV (external jugular vein),
Graft
ICA (internal carotid artery),
IJV (internal jugular vein),
Innom (Innominate artery)
InMam (inferior mammary),
Jugular,
Left
Mid
Prox (proximal),
Right
Sag (sagittal)
Sten (stenosis),
Subc (subclavian),
SupTh (superior thyroid),
SV (superior vena cava).
Trv (transverse)
Thyroid
Vert (vertebral),
Vein,
VertV (vertebral vein).

It will be observed that the words have been sorted out by their frequency of usage, with higher frequency words being listed first. Words with the same ranking and same initial letters will be saved in alphabetical order. The system will search down the list for the first word matching all of the letters typed by the user. The following Table 2 illustrates how many letters must be keyed in to get certain words:

TABLE 2

| Letter typed | Word chosen |
|---|---|
| a | Artery |
| an | Aneur |
| ana | Anast |
| ao | Aorta |
| b | Bifurcation |
| bu | Bulb |
| c | CCA |
| d | Distal |
| e | ECA |
| ej | EJV |
| g | Graft |
| i | ICA |
| ij | IJV |
| in | Innom |
| inm | InMam |
| j | Jugular |
| l | Left |
| m | Mid |
| p | Prox |
| r | Right |
| S | Sag |
| St | Sten |
| su | Subc |
| sup | SupTh |
| sv | SV |
| t | TRV |
| th | Thyroid |
| v | Vert |
| vei | Vein |
| vertv | VertV |

Ultrasound imaging systems typically have a "Set" or "Select" key, each of which is used to select certain functions or parameters, much like a left "click" made on a computer mouse. If the user-selected word appears on the screen, the user need only press the "Select" or "Set" key (although the space bar, the "Return" key or any other punctuation key could be used as well) to have the cursor jump to the end of the word. The system is then ready for the next word. The operator needs to keep typing in the letters until the desired word appears on the screen. A space is automatically added between each word.

The following Table 3 illustrates some of the words used for an abdomen annotation. The words are likewise sorted out in accordance with the order described above.

TABLE 3

| Letters typed | Chosen word |
|---|---|
| a | Aorta |
| ap | Appendix |
| b | Bladder |
| bo | Bowel |
| c | CBD. (common bile duct) |
| ca | Caudate Lobe |
| Ce | Celiac Art |
| d | Distal |
| g | GDA (gastro duodenal artery) |
| ga | Gallbladder |
| h | Hepatic Vein |
| hepatic a | Hepatic Artery |
| i | IVC (inferior vena can) |
| k | Kidney |
| l | Liver |
| le | Left |
| lo | Lower |
| lob | Lobe |
| m | Mid |
| p | Pancreas |
| po | Portal Vein |
| pr | Prox (proximal) |

TABLE 3-continued

| Letters typed | Chosen word |
|---|---|
| r | Right |
| s | Spleen |
| sa | Sag (sagittal) |
| sm | SMA (superior mesenteric artery) |
| splen | Splenic Vasculature |
| t | TRV (transverse) |
| u | Upper |
| v | Vein |

If the word is not in the memory, then the user has to type the entire word. The annotation automatic fill algorithm can also be turned on or off. When it is off, the screen is going to display whatever is typed on the keyboard. When it is on, the annotation automatic fill algorithm will anticipate the word or words that the operator wishes to insert when he or she types the first one or two letters of the word that is desired. This results in a substantial reduction of the actual amount of typing that the operator needs to perform during the ultrasound scan.

Figure 6:
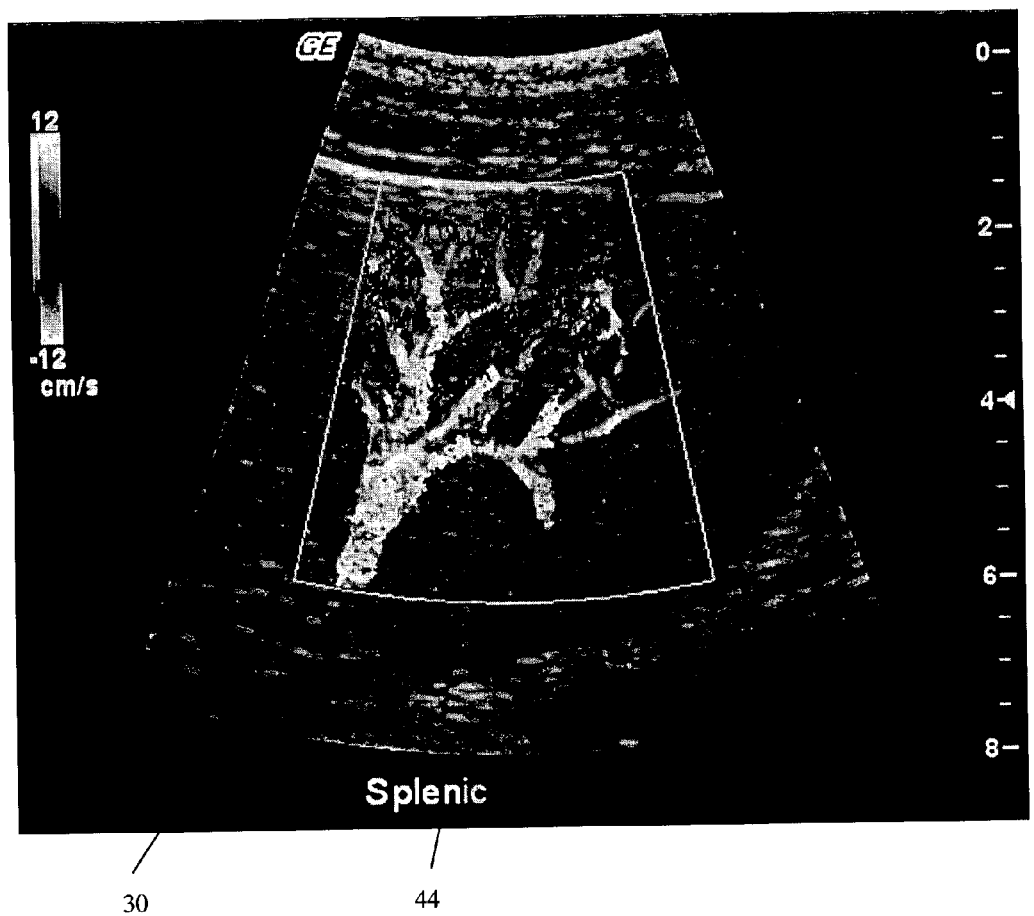
FIG. 6 is the screen display illustrated in FIG. 2 and showing the fifth letter completed by the user.
Figure 7:
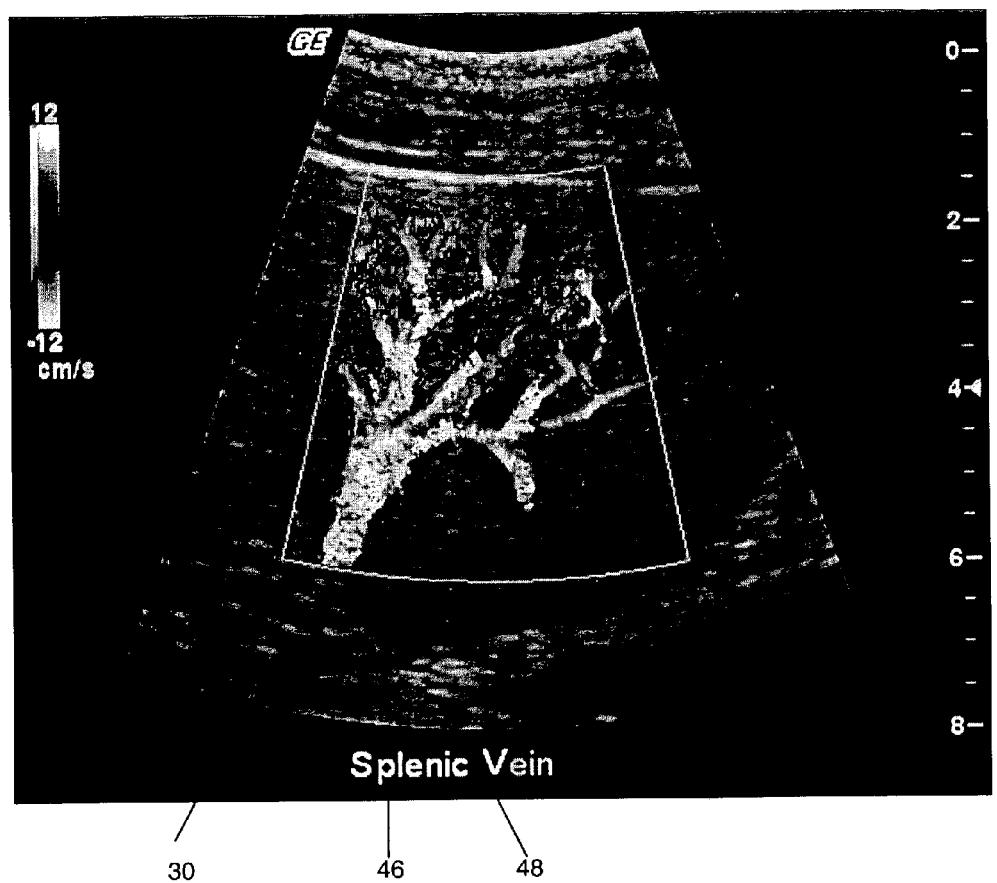
FIG. 7 is the screen display illustrated in FIG. 2 and showing the eighth letter completed by the user.
Figure 8:
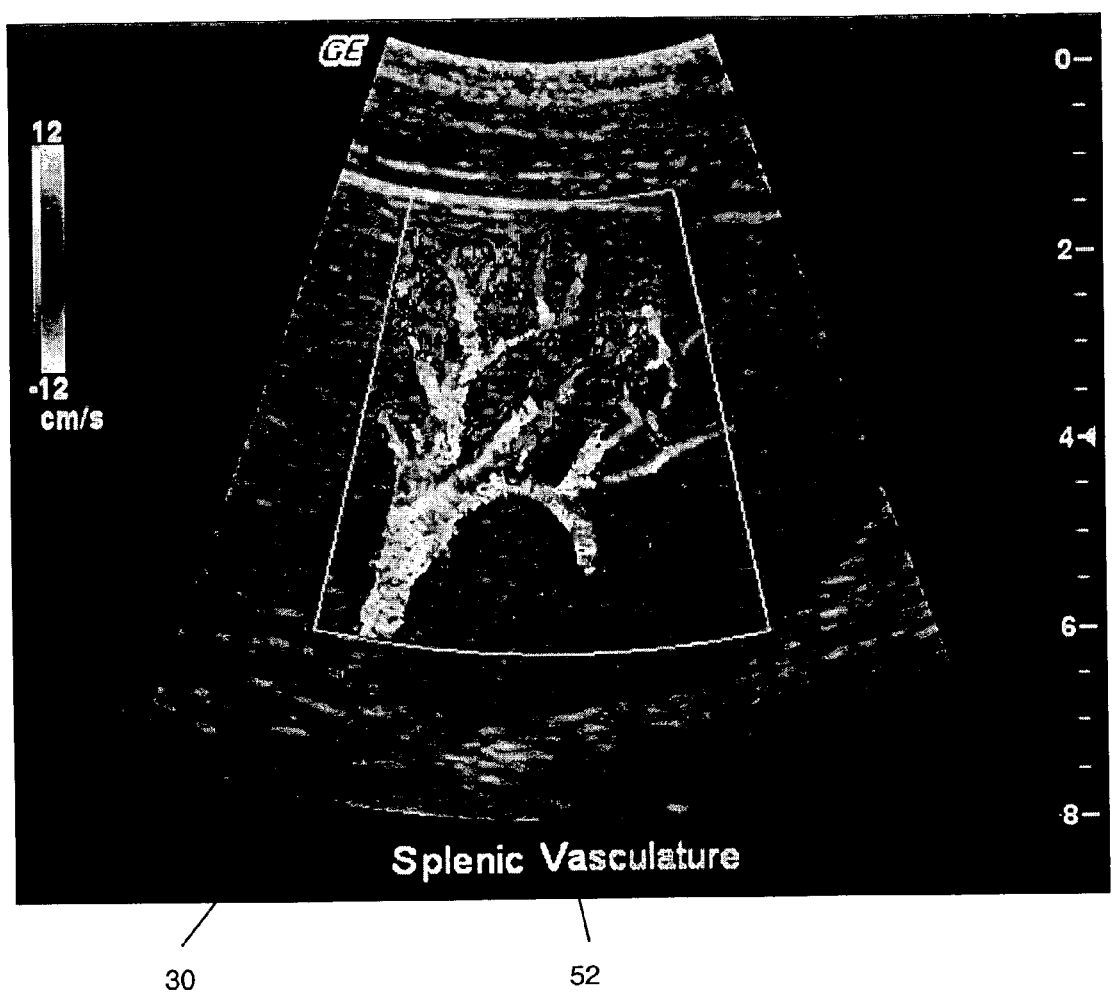
FIG. 8 is the screen display illustrated in FIG. 2 and showing the ninth letter completed by the user.
Figure 9:
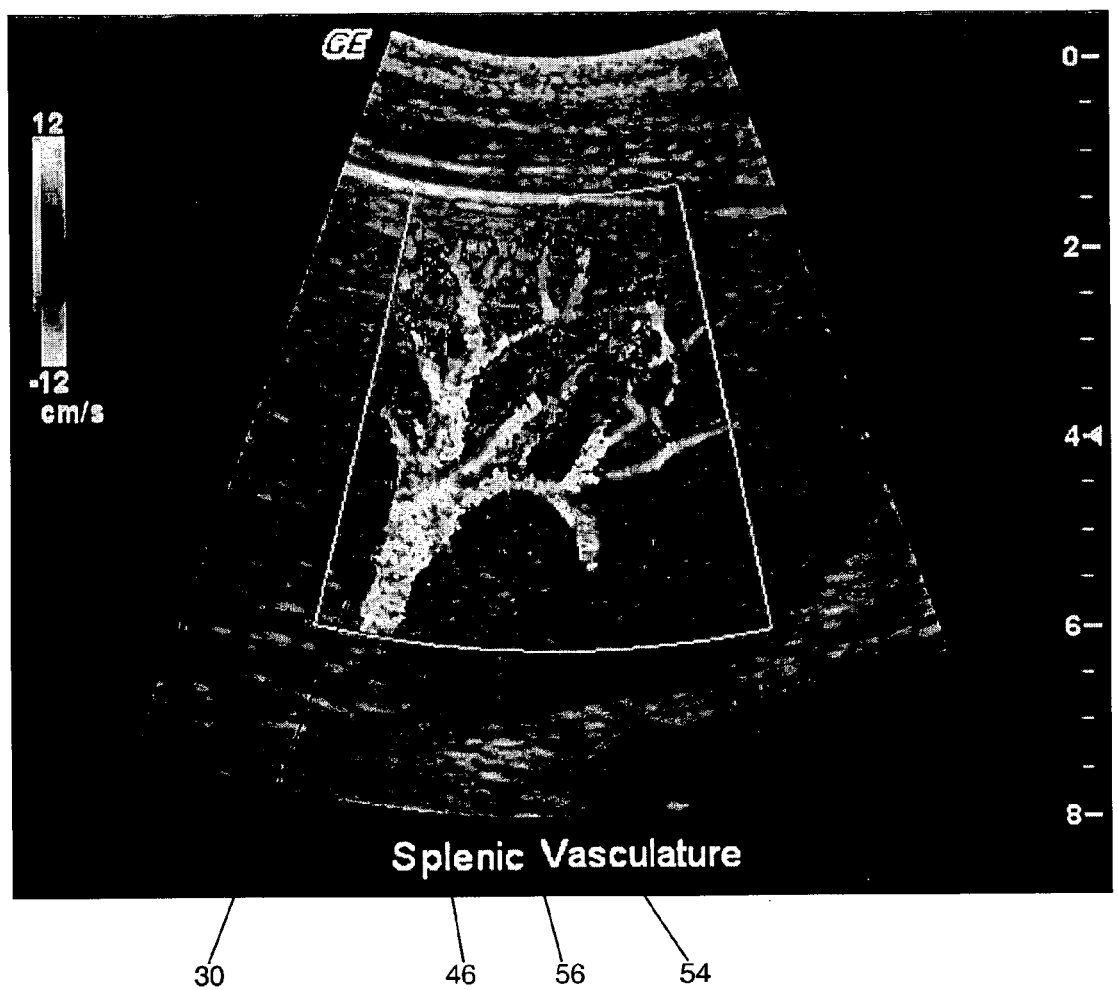
FIG. 9 is the screen display illustrated in FIG. 2 and showing the completed annotation.

In application, the sonographer is presented with a screen display 30 much like that illustrated in FIGS. 2 through 9. In this example, the sonographer is attempting to type the annotation "splenic vasculature" 46, normally a nineteen keystroke entry, in the least number of strokes possible. The annotation 32 appears at the bottom of the display 30. As shown in FIGS. 2 through 5, the user types 34 the first letter "s" and the highest ranking option to appear is the word "spleen" 36. The complete word is shown in a lighter background. Since the word "spleen" 36 is not the desired word, the sonographer continues typing the letters "p" 38, "l" 40, "e" 42 and "n" 44. In FIG. 6, it will be seen that the word "spleen" 36 no longer matches, so the highest-ranking word matching the typed letters "splen" is "splenic" 46. This complete word 46 also displays in a lighter background. In FIG. 7, the user hits the spacebar or the "set" key, which accepts the suggested word and then continues typing the first letter "v" 48 of the next word. The most likely "v" word is "vein" 50 so that is shown in the lighter background. In FIG. 8, the user types the letter "a" 52 and, since "vasculature" 54 is the most likely word matching the letters "va", that word appears in lighter background. In FIG. 9, the user hits the set key to accept the word "vasculature" 54 and the completed annotation "splenic vasculature" 56. In summary, the key presses in this example are S, P, L, E, N, space, V, A. The key count is eight, compared to nineteen keystrokes normally required. This results in a 58% reduction in the keystrokes for this example. Of course, expected efficiency and overall reduction will vary from application to application.

If the preceding example is expanded to include a drop-down box, only four keystrokes are required. After the user types "s", the most likely word "spleen" is shown as described above, and a drop-down list appears. This list contains the next three most likely matches, namely: "Sag", "SMA", and "splenic vasculature". The user must hit the down arrow three times to highlight the last suggestion ("splenic vasculature") and then hit the "set" key. This results in a 79% improvement over typing the entire word.

In accordance with the method of the present invention, the ultrasound operator has four options. The speech recognition apparatus can be activated, the auto annotation filler can be activated, both can be in use or neither can be in use.

In accordance with the method of the present invention, there are three methods to annotate the image by voice. Two permit free form text entry (dictation) using a general medical dictation vocabulary; one requires the user to enter a dictation mode, while the other adds a keyword before each comment. The third method involves selection from a limited list of terms. Each of these methods assumes that the sonographer is already using speech recognition to control the ultrasound machine.

There are several features common to all of these methods. First, comments and annotations can be positioned on screen with a command "Move Comment Top Left" or "Move Comment Bottom Center." The commands "Return" or "New Line" set a carriage return. Words can be deleted with commands like "Word Delete" or all annotations can be erased with "Delete All" or "Clear All."

Secondly, spaces are automatically inserted between words; other punctuation must be listed at the point where it should be inserted. The name of the punctuation symbol should be verbalized. A word can be capitalized by preceding it with the command "Capital", "Cap", or by saying "Capitalize That" or "Cap That" after it is typed. To capitalize all letters, the caps lock key on the keyboard must be depressed.

Additionally, words can be spelled instead of spoken. However, in order to avoid confusion with words that sound similar to the name of a letter, the user can precede the letters with the command "Spell" or "Type Letters" followed by all of the letters with little or no time gap between them.

The first method for verbal annotations involves a medical dictation recognition engine. Generally, the ultrasound machine that operates from speech commands is already listening for system commands and ignores other speech. Therefore, the user must separately issue a verbal command to instruct the machine to take dictation. This command enables the grammar dictionary and instructs the software to transcribe everything the user says. Similarly, a command is required to instruct the machine to stop transcribing. Other commands are required for correcting errors in dictated text, punctuation and spacing. A sample interaction is described in Table 4 below.

TABLE 4

| User Says | Machine Reaction |
|---|---|
| <keyword> Type | Machine enables dictation engine |
| Left Coronary Artery | Types "Left Coronary Artery" in last position cursor was in. |
| New Line | Moves to next line |
| Note Blockage Exclamation Point | Types "Note blockage!" |
| Move Comment to Top Left | Positions text on top left side of screen |
| Done | Machine disables the dictation engine. |

In the foregoing example, <keyword> refers to a specific word used to identify a command to the machine. This is an optional feature that improves the accuracy of the dictation. In the event the machine transcribes inaccurately, or the user makes an error, the sonographer can say correct <error> to <correction> to have the machine fix the mistake.

The second method also uses a dictation recognition engine but it does not require the user to enter a special dictation mode. Instead, comments are prefaced with a keyword such as "Type." This eliminates the need for the user to enter a separate mode to get the machine to transcribe. It also makes use of the correction commands described for method one. A sample interaction using this third method is described in Table 5 below.

TABLE 5

| User Says | Machine Reaction |
|---|---|
| Type Left Coronary Artery | Machine types "Left Coronary Artery" in last position cursor was in. |
| New Line | Moves to next line |
| Type Note Blockage Exclamation Point | Types "Note Blockage!" |
| Moves Comment to Top Left | Positions text on top left side of screen. |

The third method of speech recognition is the restricted list method. It uses a command control recognition engine, and requires every possible annotation word to be in a pre-defined list. This list of words can be user defined and context sensitive to the type of exam being performed. The grammar definition for this method is of the form <keyword> <wordlist>[+], where <keyword> identifies the phrase as a comment (for example "Type"), and <wordlist> is one or more words from the list.

For example, if the sonographer issues a verbal command "Type left coronary artery", and provided the words "Left", "Coronary" and "Artery" are in the available word list, the system types them on the screen display. As such, the transcription feature becomes another command in the list of commands that the system understands.

A partial list of the grammar entries for a general exam are the following words: Right, Left, Top, Bottom, Of, And, etc. If the sonographer wished to perform an examination of the carotid artery, the sonographer would select the carotid wordlist, which could include terms such as: aneurysm, anastamosis, aortic arch, bifurcation, bulb, common carotid artery etc. The sonographer would need to train the system for each such exam before the speech engine would recognize the terms. After the system is trained using the above grammar, the system would respond to the command "Type Left Aneurysm" because each of the terms is within its grammar lists. It would not respond to "Type Left Side Aneurysm" because the word "Side" is not in the list.

The speech recognition method of the present invention employs several different elements as are well known in the art. For example, any microphone suitable for speech recognition may be used. Additionally, any mounting option for the microphone can be used. Furthermore, the microphone could be either wired directly to the speech recognition system or a wireless connection could be used.

There are also many types of speech recognitions systems known to the art that could be used in the method of the present invention. For example, the speech recognition system could use a processor embedded within the housing of the ultrasound unit. The speech recognition system could also be installed on a stand-alone processor connected to the ultrasound machine.

Obviously, the computer must be connected to the ultrasound in some way. These types of connections are also standard and are well known in the art. The present invention is not limited to a certain type of ultrasound or to a specified computer. It is instead recognized that the method of the present invention is designed for use with all types of speech recognition systems and ultrasound machines.

Referring now to FIG. 1, it shows the flow chart of the automatic annotation filler in accordance with the present invention. As can be seen from FIG. 1, the voice recognition system and the keyboard can work independently and concurrently. The automatic annotation filler is generally identified 10. The schematic representation includes a keyboard 12 and an ultrasound image display monitor 14. The first question asked by the method is whether the automatic annotation filler is "on" 22. If the automatic annotation filler is "off" then the display 14 merely shows what the user types on the keyboard. A second question asked is whether the speech recognition is "on" 28. If the speech recognition is "on" then the display monitor 14 shows what the user says by voice. If the automatic annotation filler is not on, the display monitor 14 does not automatically show the annotation unless the keyboard 12 is manually operated. If the automatic annotation filler 22 is on, then the application is read in 24 and the search words in the memory 26 are electronically accessed to display the automatic annotation included on the display monitor 14. In other words, the ultrasound operator can both type and use vocal commands to enter the annotations required for the ultrasound imaging and the display 14 will show the most likely word that the sonographer intends to type based on the keys he or she has already hit or the words he or she has spoken.

It is to be understood that the invention is not limited to the embodiment set forth herein but that the invention may be carried out in other ways without departure from the spirit of this invention.

What is claimed is:

1. A method for annotating a displayed ultrasound image using commands comprising the steps of:
    providing an annotation vocabulary sorted in descending order of usage frequency;
    providing a method to select a subset of words from the vocabulary that are relevant to the imaged anatomy;
    detecting the initial command;
    selecting a suggestion list from the selected subset of words from the vocabulary; and
    displaying the suggestion list to the user for optional acceptance or further specification.

2. The method of claim 1 wherein the commands comprise keyboard entries corresponding to partial annotations.

3. The method of claim 2 wherein the vocabulary is comprised of words and word pairs that are commonly used in annotations.

4. The method of claim 3 wherein the vocabulary is dynamically generated from words typed into the system.

5. The method of claim 1 wherein the usage frequency of each entry in the vocabulary list is updated dynamically based on usage on the system.

6. The method of claim 1 wherein each entry in the vocabulary is associated with one or more subvocabularies.

7. The method of claim 6 wherein each entry has an independent frequency related to usage with each subvocabulary.

8. The method of claim 7 wherein each independent frequency is dynamically updated based on system usage.

9. The method of claim 8 wherein the suggestion list is determined from all entries in the selected subvocabulary that have a partial match with the command characters entered.

10. The method of claim 9 wherein the partial match includes all characters of the command entered, and at least the first character of the vocabulary entry.

11. A method for annotating a displayed ultrasound image using commands comprising the steps of:
    providing an annotation vocabulary sorted in descending order of usage frequency;
    providing a method to select a subset of words from the vocabulary that are relevant to the imaged anatomy;
    detecting an initial command to annotate an image;

selecting a suggestion list from the selected subset of works from the vocabulary; and displaying the suggestion list to the user for optional acceptance or further specification detecting an annotation; and transcribing the annotation onto the image.

12. The method of claim 11 wherein the initial command consists of a keyword.

13. The method of claim 11 wherein the initial command is issued by a voice, keyboard or system state changing device.

14. The method of claim 13 wherein the body of the annotation is detected using a speech recognition technique.

15. A method for using a keyboard to initiate the annotation of ultrasound images comprising the steps of:

providing a main directory of annotations corresponding to each of the scans an ultrasound machine is likely to perform;

providing a sub-directory of annotations likely to be used in the context of an ultrasound scan for item in the main directory;

detecting at least one signal from the keyboard command and selecting from the main directory of annotations;

detecting at least one signal from the keyboard command and selecting one or more appropriate complete annotations corresponding to the subdirectory and the signal;

displaying the annotations on the ultrasound image.

16. A system for annotating a displayed ultrasound image using initiating commands comprising:

means for providing a vocabulary of commands specifying the anatomy being scanned, said vocabulary including a number of sub-vocabularies, wherein each of the sub-vocabularies contains a list of commands relevant to the anatomy being scanned;

means for detecting a signal from at least one command;

selecting at least one of the sub-vocabularies in response to the command;

selecting at least one annotation from the at least one subvocabulary, and displaying the annotation corresponding to the command.

17. The system of claim 16 wherein the system includes means for permitting commands in the form of keyboard entries corresponding to annotations and means for permitting commands in the form of voice commands.

18. The system of claim 17 wherein the system includes means for permitting operation by keyboard entry concurrently with voice commands.

19. The system of claim 16 wherein said signal detecting means includes means for recognizing a spoken voice command and translating the spoken voice command into said signal using the subvocabulary.

20. The system of claim 16 including a plurality of voice command determining states, each of said states corresponding to one sub-vocabulary, wherein said selecting steps select a sub-vocabulary that corresponds with the voice command.

21. A system for using keyboard commands to annotate ultrasound images comprising: means for providing a vocabulary of commands for inserting annotations on an ultrasound image;

means for providing a sub-vocabulary of commands for inserting annotations on an ultrasound;

means for detecting at least one signal from a command and selecting the sub-vocabulary associated with the command;

means for detecting at least one signal from a command and selecting the associated annotation;

means for placing the annotation in the appropriate location on the ultrasound image and means for displaying the annotation an the image.

22. The system of claim 21 including means for processing voice commands and wherein the system permits keyboard entries corresponding to annotations to be entered concurrently with voice commands.

23. The system of claim 22 wherein the system permits operation by a non-voice activated device concurrently with a voice commands.

24. The system of claim 23 wherein said detecting means includes means for recognizing a spoken voice command and translating the spoken voice command into said signal using the subvocabulary.

25. The system of claim 24 wherein said ultrasound system has a plurality of voice command determining states, each of said states corresponding to one sub-vocabulary, wherein said selecting means includes means for selecting a sub-vocabulary that corresponds with the voice command.

26. A system for using keyboard commands to annotate ultrasound images comprising:

a main directory of annotations corresponding to each of the scans and ultrasound machine is likely to perform;

one or more sub-directories of annotations likely to be used in the context of an ultrasound scan for item in the main directory;

means for detecting at least one signal from at least one keyboard command;

means for selecting from the main directory of annotations;

means for detecting at least one signal from the keyboard command and selecting the appropriate annotation corresponding to the subdirectory and the signal; and means for displaying the annotation with the ultrasound image.

* * * * *